United States Patent [19]

Wood et al.

[11] Patent Number: 4,998,826

[45] Date of Patent: Mar. 12, 1991

[54] AGRICULTURAL INFRARED THERMOMETER

[75] Inventors: Don E. Wood, Irvine; Wayne Scharf, Silverado, both of Calif.

[73] Assignee: Telatemp Corporation, Fullerton, Calif.

[21] Appl. No.: 278,754

[22] Filed: Nov. 30, 1988

[51] Int. Cl.$^5$ .......................... G01J 5/10; G01K 7/00; G01K 1/14

[52] U.S. Cl. .................................. 374/129; 374/121; 374/124; 250/334

[58] Field of Search ...................... 374/124, 129, 121; 250/334; 356/43; 364/557

[56] References Cited

U.S. PATENT DOCUMENTS

| | | | |
|---|---|---|---|
| 3,715,497 | 2/1973 | Cooper et al. | 250/334 |
| 3,718,757 | 2/1973 | Gulitz et al. | 374/124 |
| 3,821,895 | 7/1974 | Sumikawa et al. | 374/124 |
| 3,933,044 | 1/1976 | Loper et al. | 250/334 |
| 4,142,417 | 3/1979 | Cashdollar et al. | 374/123 |
| 4,218,707 | 8/1980 | Reed et al. | 250/334 |
| 4,343,182 | 8/1982 | Pompei | 374/129 |
| 4,378,701 | 4/1983 | Mountain et al. | 374/121 |
| 4,502,793 | 3/1985 | Smith et al. | 374/124 |
| 4,566,808 | 1/1986 | Pompei et al. | 374/124 |
| 4,626,686 | 12/1986 | Pompei et al. | 374/124 |
| 4,682,222 | 7/1987 | Smith et al. | 250/334 |
| 4,724,482 | 2/1988 | Duvent | 250/334 |
| 4,728,804 | 3/1988 | Norsworthy | 250/334 |
| 4,797,840 | 1/1989 | Fraden | 374/133 |
| 4,840,496 | 6/1989 | Elleman et al. | 374/124 |

FOREIGN PATENT DOCUMENTS

| | | | |
|---|---|---|---|
| 56-21025 | 2/1981 | Japan | 250/334 |
| 59-15379 | 1/1984 | Japan | 250/334 |
| 63-38192 | 2/1988 | Japan | 250/334 |
| 2073537 | 10/1981 | United Kingdom | 250/334 |

OTHER PUBLICATIONS

Watson, J. L. et al., "A New Scanning Thermometer," J. Phys. E (GB), vol. 4, No. 12 (Dec. 1971).
Burke, J. J., Mahan J. R., and Hatfield, J. L., "Crop-Specific Thermal Kinetic Windows in Relation to Wheat and Cotton Biomass Productions", *Agronomy Journal*, vol. 80, No. 4, Jul.-Aug. 1988, pp. 553-556.
Burke, John J., and Hatfield, Jerry L., "Plant Morphological and Biochemical Responses to Field Water Deficits", Plant Physiology, vol. 85, 1987, pp. 110-103.
Hatfield, J. L., "Research Priorities in ET: Evolving Methods", *Transactions* of the ASAE, vol. 31, No. 2, 1988, pp. 490-495.
Hatfield, J. L., Burke, J. J., Mahan, J. R., and Wanjura, D. F., "Foliage Temperature Measurements: A Link Between the Biological and Physical Environment", *International Conference on Measurement of Soil and Plant Water Status*, vol. 2, Jul. 6-10, 1987.

(List continued on next page.)

*Primary Examiner*—William A. Cuchlinski, Jr.
*Assistant Examiner*—Diego F. F. Gutierrez
*Attorney, Agent, or Firm*—Knobbe, Martens, Olson & Bear

[57] ABSTRACT

An infrared thermometer has a field of view selected so that the temperature of the crop growing in a field is accurately measured. The infrared thermometer may be mounted on a support pole in a field to substantially continuously monitor the foliage temperature of the growing crop. In one preferred embodiment, the infrared thermometer comprises and instrument housing structure provided with an infrared telescope mounted on a turntable that scans through an angle of the field, while an electronic circuit simultaneously integrates the output of the infrared telescope. The angle to be scanned is selected by the user in accordance with his needs. In another embodiment, the infrared thermometer comprises a novel sensor head block including an aperture which provides a wide, elongated oval field of view for an infrared sensor provided therein. In both embodiments, the elongated oval field of view has a width that is at least four times its height. The elongated oval field of view is selected to substantially block the infrared radiation emitted by background sources such as the sky and the ground.

12 Claims, 8 Drawing Sheets

OTHER PUBLICATIONS

Upchurch, Dan R., and Mahan, James R., "Maintenance of Constant Leaf Temperature by Plants I. Hypothesis–Limited Hemeothermy", 18 pages, (publication data unknown), (undated).

Upchurch, Dan R., and Mahan, James R., "Maintenance of Constant Leaf Temperature by Plants II, Experimental Observations in Cotton", 25 pages (publication unknown), (undated).

Telatemp Corporation, Fullerton, CA., Model AG-42 Infrared Thermometer (Nov. 1981).

Telatemp Corporation, Fullerton, CA., Model 50 Large Area Infrared Thermometer (undated).

Telatemp Corporation, Fullerton, CA., Model 2100 Infrared Three-mode Temperature Control System, (Dec. 1984).

Telatemp Corporation, Fullerton, CA., CWSI Data Logger (undated).

Everest Interscience, Inc., The Infrared AG Multimeter, including the Model 510 and the Series 4000, (undated).

Standard Oil Engineered Materials Company, Scheduler ® Plant Stress Monitor (undated).

Dexter Research Center, Inc., Dexter, Michigan, Model 1M Thermopile Detector (Aug. 86).

Dexter Research Center, Inc., Dexter, Michigan, Model 2M Thermopile Detector (Aug. 86).

Dexter Research Center, Inc., Dexter, Michigan, Application Briefs 1,2,3, and 4, (Jul. 1978).

AGRICULTURAL INFRARED THERMOMETER

BACKGROUND OF THE INVENTION

1. Field of the Invention

The present invention relates to devices for measuring temperatures of remote objects, and more particularly to devices for measuring temperatures of crops growing in a field.

2. Prior Art

In recent years, agricultural researchers have had considerable interest in accurately measuring the temperature of crops growing in a field. It has only recently been discovered that the foliage temperature of a plant is directly related to the growth rate. Specifically, it has been discovered that for any given type of plant, there is a narrow foliage temperature range, or a thermal kinetic window, within which the plant will achieve optimum yield and biomass production. Researchers in the field are currently studying the thermal kinetic window of various crops. Such information can be used by a farmer desiring to produce the largest possible harvest. To do this, the farmer attempts to maintain the foliage temperature within this thermal kinetic window for as long as possible to maximize biomass production.

The temperature of plant foliage is dependant upon several factors including the ambient air temperature, wind speed, humidity, solar output and soil water content. As each day in a growing cycle begins, the foliage temperature is typically well below the thermal kinetic window, which is the optimum temperature for biomass production, essentially tracking the ambient air temperature. As the day progresses, the foliage temperature begins to rise as the sun radiates into the field, and the air temperature increases. During the course of a sunny day, the temperature of the ambient air may rise up to and even above the thermal kinetic window. If the foliage temperature were to rise a substantial amount above the thermal kinetic window, the crop may be considered "stressed", in which case the foliage may wilt within a few days, and crop production will suffer due to a decrease in biomass production.

To minimize crop stress caused by an increase in foliage temperature above the thermal kinetic window, additional water is provided to the crop primarily by irrigation. Researchers have found that plants have a capacity (although limited) to maintain their temperature within the thermal kinetic window during periods of increased ambient air temperature. That is, while previously it was thought that plants were "poikilotherms", which means that foliage temperature simply follows the temperature of the environment, it has been discovered that most plants are actually "homeotherms" to a limited extent. A "homeotherm" tries to maintain a temperature within a specified range, similar to a human which for example attempts to maintain the temperature at 98.6° F. Specifically, most plants have a capacity to reduce their temperature by as much as several degrees, in order to maintain a temperature within the thermal kinetic window. To that extent, a plant may be considered a homeotherm. Although plants do have a capacity to reduce their temperature, they have no capacity to raise their temperature, so to that extent they are poikilotherms.

Transpiration, a process comprising the evaporation of water from the surface of the foliage, is an significant method by which a plant can reduce its temperature. In other words, if adequate soil moisture is available the plant can cool itself by several degrees through transpiration in an attempt to maintain its temperature within the optimum temperature range. It has been reported that the temperature within a "crop canopy", which includes air surrounding the leaves cooled by transpiration, may be several degrees below the air temperature, thereby indicating the ability of crops to cool themselves. By reducing the length of time that the crops are subjected to stress caused by elevated temperatures and a lack of soil moisture, an increase in biomass and crop production is possible.

However, since it is often very difficult to determine the amount of water that is sufficient for optimum plant cooling, a farmer may tend to over- or under-water his crop or may fail to apply water at critical times throughout the growing season. Previous methods for calculating the optimum amount of, and time for, irrigation necessary for a given crop required using a complex algorithm that took into account various factors including canopy temperature, air temperature, wind speed, humidity and solar output. Further complicating the watering decision, water may be in short supply or simply unavailable, particularly in periods of drought. Under these conditions, water management is of utmost importance.

Water management is also particularly important to farmers in geographical areas that lack substantial rainfall. In the Western United States, large agricultural concerns rely upon irrigation for all their water needs, and therefore, water is a very precious commodity and efficient management of the water is an absolute necessity for agricultural endeavors.

To maintain optimum crop production by reducing or eliminating crop stress, the farmer must balance the availability and cost of water against his estimate of the needs of the crop. Without detailed knowledge of the foliage temperature of the crop, and without even limited knowledge of the optimum temperature range for his particular crop, the farmers' estimates of the water needs for his crop are often haphazard guesses as to the necessary amount or timing. Thus, there exists a high probability that the crops will not be sufficiently watered for optimum cooling, or will be watered in wasteful quantities.

A farmer having a continuous and accurate measure of crop temperature can immediately respond to the water needs of his crop long before crop damage becomes visibly apparent. If, for example, he observes a decrease in the ability of the crop to effectively cool itself, he will know that more water is needed. If, on the other hand, he observes that the crop is cooling itself effectively, he will know that the crop has sufficient water, and that no more is needed. In times of limited supply, he can use the temperature information to allocate the available water among competing uses and therefore efficiently manage crop growth.

Furthermore, the data obtained regarding foliage temperature may also be used to assist in detecting plant disease. Diseases can cause the plant's stomates or pores through which transpiration occurs, to clog, thereby causing an increase in plant temperature and a corresponding decrease in biomass or crop production.

By correlating knowledge of the individual crop's thermal kinetic window with the foliage temperature, the quantitative degree of plant stress may be readily determined. However, quantification of plant stress in the field is often difficult because of the need to obtain multiple daily measurements of a wide area of plant foliage temperature. Individual foliage temperature measuring devices, such as thermocouples attached directly to the plant are thus an impractical means of obtaining foliage temperature data. Infrared thermometers have been generally employed by the agricultural industry to remotely determine the foliage temperature. Therefore, by measuring the temperature differential between the ambient air temperature and the foliage temperature, a factor relating to the stress of the crop may be determined by the farmer. If stress is indicated, then additional water may be added to the soil through irrigation.

It has been suggested that an infrared thermometer be incorporated in a computer-based sYstem located in the field. This system can measure the crop canopy temperature, air temperature, wind speed, humidity and solar output. Using these measurements, the computer can estimate the crop stress factor.

Typical infrared thermometers utilized to measure foliage temperature have a conical 15° field of view, although instruments having a conical field of view ranging from 4° to 60° are commercially available.

The conical field of view poses a problem for one who wishes to obtain one measurement indicative of the average temperature of the foliage in the field. An infrared thermometer with a narrow field of view can be pointed at one particular place in the field, and a measurement indicative of the temperature at that place can be accurately obtained. However, this measurement may not be indicative of the temperature of the foliage at other places in the field. Thus there is a need for an infrared thermometer with a wide field of view, that receives radiation from a large portion of the field, and provides an output indicative of the average temperature of the foliage in the field.

Infrared thermometers with a conical field of view, such as those currently available, do not satisfy this need. Some may provide a wide field of view, but when used to make temperature measurements, there is an accuracy problem. The difficulty is that the infrared radiation within the wide circular area of the conical field of view of these infrared thermometers often includes background radiation from sources such as the soil and the sky. With this unwanted background radiation incident upon the infrared sensor, the temperature measurements are affected and therefore inaccurate to some degree.

SUMMARY OF THE INVENTION

The present invention provides an infrared thermometer that continuously and accurately monitors the crop foliage temperature and provides an accurate measure of the foliage temperature throughout the day. With this information, the farmer can accurately assess the water needs of his crop, and accordingly water it as needed. The foliage temperature data may be used to maximize productivity of the crop land by increasing plant biomass and crop yield while at the same time eliminating wasteful and ineffective watering. Thus, using the present invention, a farmer can practice more effective and efficient water management.

The infrared thermometer of the present invention may be mounted on a support pole in a field to substantially continuously monitor the foliage temperature of the growing crop. The infrared thermometer provides precise readings whereby the effectiveness of the farmer's irrigation program may be easily, quickly and readily ascertained. The infrared thermometer may comprise a personal computer or other means for storing, at periodic time intervals, the temperature measurements.

In one preferred embodiment, the infrared thermometer may be housed in an instrument housing structure provided with a protective window that substantially transmits infrared radiation. The window permits the transmission of infrared radiation emitted from the crop foliage to enter the instrument housing structure where it is detected by the infrared thermometer, which includes an infrared telescope assembly. The infrared telescope may, for example, be a Cassegrain infrared telescope having a conical field of view from 4° in some models to 15° in other models.

To permit wide coverage of the field in which the crop is growing, the infrared telescope is mounted on a turntable which rotates the infrared telescope through a selected angular rotation. Because the infrared telescope is rotated with the turntable, the infrared telescope itself may have a relatively restricted field of view yet still measure a large area of the field. The angular range of the turntable is adjustable so that the infrared telescope can selectively scan any angle up to the angle permitted by the protective window.

In another preferred embodiment, an infrared thermometer is disclosed having a wide field of view while not requiring a turntable. In this embodiment, a novel sensor head block advantageously allows a wide, rectangular field of view for an infrared sensor provided therein.

The sensor head block includes an aperture which defines the angles of the field of view seen by the infrared sensor. Thus, the limits of the field of view are determined by the geometry of the sensor head block. In the preferred embodiment, the field of view is rectangular, specifically being 4° in height and 50° in width. The rectangular field of view is preferred, because it is able to substantially block the infrared radiation emitted by background sources such as the sky and the ground, while transmitting radiation emitted by the crop.

The sensor head block comprises a material that is thermally conductive. Furthermore, the sensor head block is preferably insulated with a low emissivity material so as to substantially eliminate temperature gradients occurring therein. The material lining the aperture of the block preferably comprises a material of known emissivity so that the infrared radiation emitted by the block is a known function of the temperature of the block. Finally, a temperature sensor is connected to the block to measure the block temperature. Using this information, an electronic circuit compensates for the temperature of the block and provides an accurate output indicative of the temperature of the crop.

DETAILED DESCRIPTION OF THE INVENTION

The invention is best understood by reference to the figures wherein like parts are designated with like numerals throughout.

Figure 1:
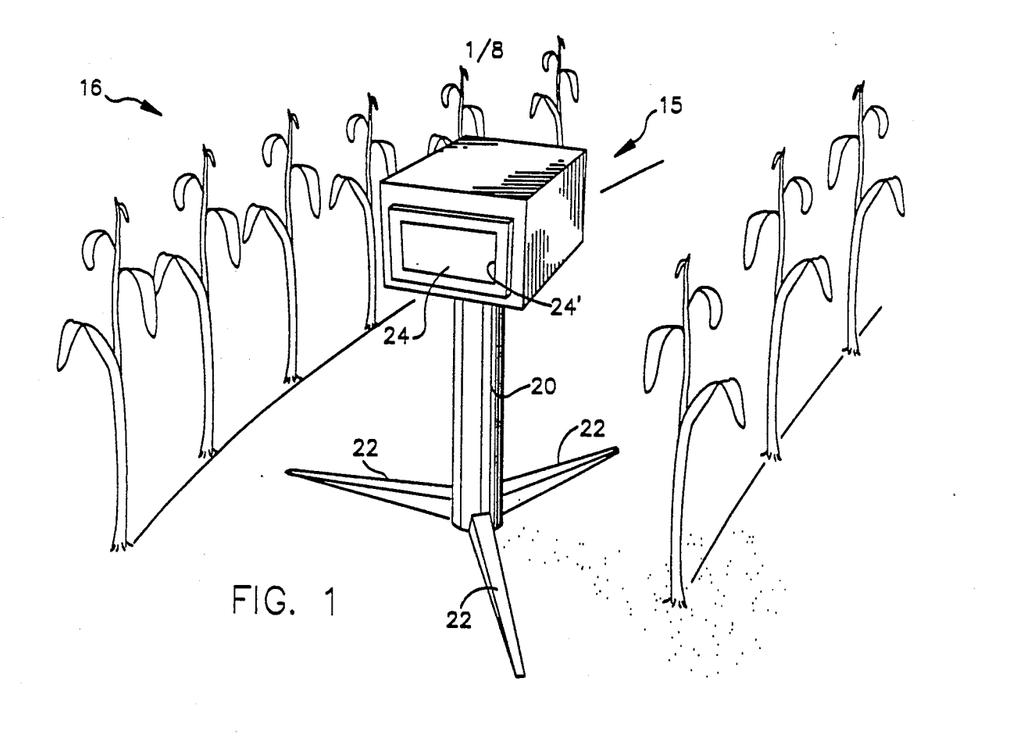
FIG. 1 shows a perspective view of one embodiment of agricultural foliage infrared thermometer mounted on a stand in a field whereby the foliage temperature may be continuously monitored.

Referring to FIG. 1, the infrared temperature sensing system shown generally at 15 may be placed in a field to monitor the foliage temperature of a growing crop 16. The infrared temperature sensing system 15 is shown including an instrument housing structure 18 mounted on a support pole 20. The support pole 20 is maintained in an upright position by a plurality of feet 22. Alternatively, the feet 22 may be removed and the support pole 20 anchored by burying a portion of the pole in the ground.

The instrument housing structure 18 is provided with an infrared transmitting protective window 24 located in an a aperture 24' which is located on one of the plurality of vertical faces of the structure 18. As best illustrated in FIG. 1, the window 20 has a generally rectangular shape. The window 24 permits the transmission of infrared radiation emitted from the crop foliage to enter the instrument housing structure 18.

Either of two alternative embodiments may be provided within the housing structure 18. The first embodiment comprises a scanning infrared telescope whereas the second embodiment comprises a stationary wide angle field of view infrared temperature sensing system. Both embodiments are described in detail below.

DETAILED DESCRIPTION OF THE SCANNING SENSING SYSTEM EMBODIMENT OF FIGS. 2, 3, 4 AND 5

Figure 2:
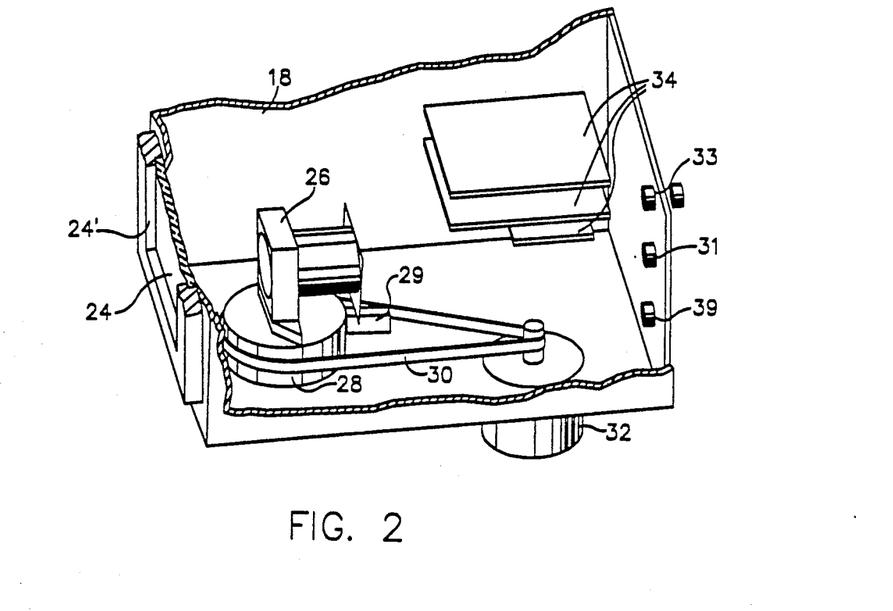
FIG. 2 is a cut-away view of an instrument housing structure in accordance with one embodiment of the present invention.

The interior of the instrument housing structure 18 is shown in the cut-away view of FIG. 2 where the top and one of the side walls of the structure 18 have been removed to reveal one embodiment of the present invention. The interior of the structure 18 includes the instrumentation necessary to provide the means capable of measuring the foliage temperature of a crop growing in a field. In this embodiment, the instrumentation comprises a scanning infrared telescope assembly 26 and a turntable 28, upon which the infrared telescope 26 assembly is mounted. The turntable 28 is capable of being rotated through a selected angular rotation by a belt 30 which is driven by a scan motor 32. Because the infrared telescope 26 is mounted on the turntable 28, the infrared telescope 26 is also rotated through the same angular displacement as is the turntable 28. The angular range of the turntable 28 is determined by an electronic assembly 34, comprising a plurality of electrically interconnected circuit boards, powered by any conventional power supply, such as batteries (not shown). The electronic assembly 34 is connected to the conventional scan motor 32 and the scan limit switches 29, so that the electronic assembly 34 controls the scan motor 32, and monitors the angular movement by the scan limit switches 29. The speed of the scan may be generally selected by a scan speed selector 31, which is electrically connected to the electronic assembly 34.

Infrared telescopes such as the infrared telescope 26 are commercially available, for example, the infrared telescope 26 is essentially the same as the infrared telescope included in the Model AG-42 infrared thermometer commercially available from Telatemp Corporation, P.O. Box 5160, Fullerton, CA. However, infrared telescopes are generally capable of only a conical field of view of typically 4° in some models to 15° in other models. Because the field of view of the infrared telescope 26 is substantially less than the typically selected angle of rotation of the turntable 28, the rotation of the turntable 28 increases the area of the field containing the crop that is subjected to temperature measurement by the infrared telescope 26. The addition of the turntable 28 therefore provides controlled movement of the infrared telescope 26 whereby it is possible to monitor a generally elongated oval area (rectangular with rounded corners) that is greater than the field of view of the infrared telescope 26 alone. The conical field of view provided by the infrared telescope 26 alone which defines the height of view of the system 15, may be narrower than one-fourth of the width of the angle scanned. In other words, the width of the angle scanned is at least four times as large as the height defined by the conical field of view. Preferably, the conical field of view of the infrared telescope is from 4° to 6°, and the angular movement of the turntable is 50°. However, it will be apparent to those skilled in the art hat a larger angular movement is obtainable if the window 24 were expanded to permit a larger scanning area for the telescope 26.

The output of the infrared telescope 26, which is provided to the electronic assembly 34, is integrated by the electronic assembly 34 for each sweep through the selected angular rotation of the turntable 28. The integration time constant may be selected by an integration time constant selector 39, which is electrically connected to the electronic assembly 34. The electronic assembly 34 comprises a circuit (not shown) which provides an output, available through a port 33, responsive to the temperature of the crop scanned by the infrared telescope 26. The electronic assembly 34 is essentially identical to the electronic assembly provided on the Model 50 Large Area Infrared Thermometer commercially available from Telatemp Corp, Fullerton, CA., with the addition of an integrator to be described. The electronic assembly 34 may also include a data storage device 35 for periodically storing temperature data.

Figure 3:
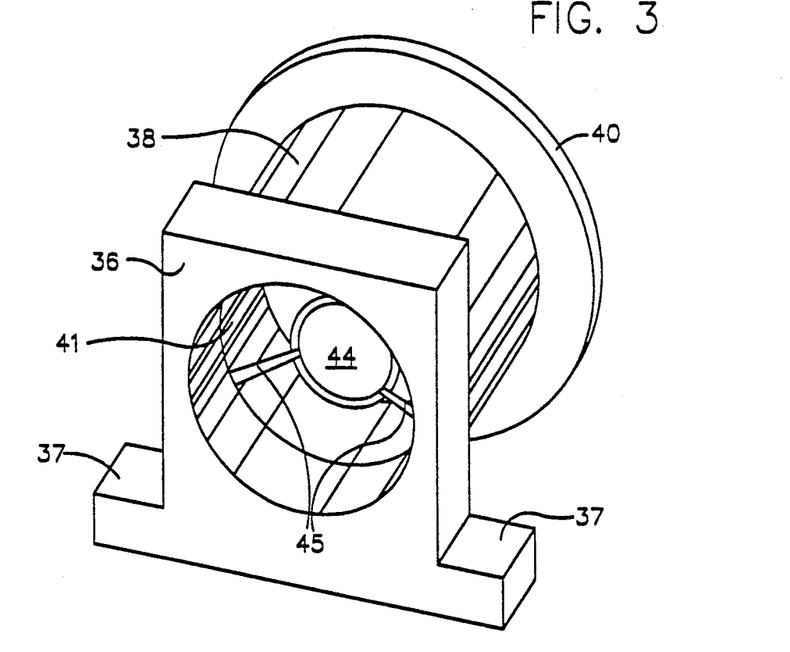
FIG. 3 is a perspective view of a commercially available embodiment of a Cassegrain infrared telescope used in a preferred embodiment of the present invention.
Figure 4:
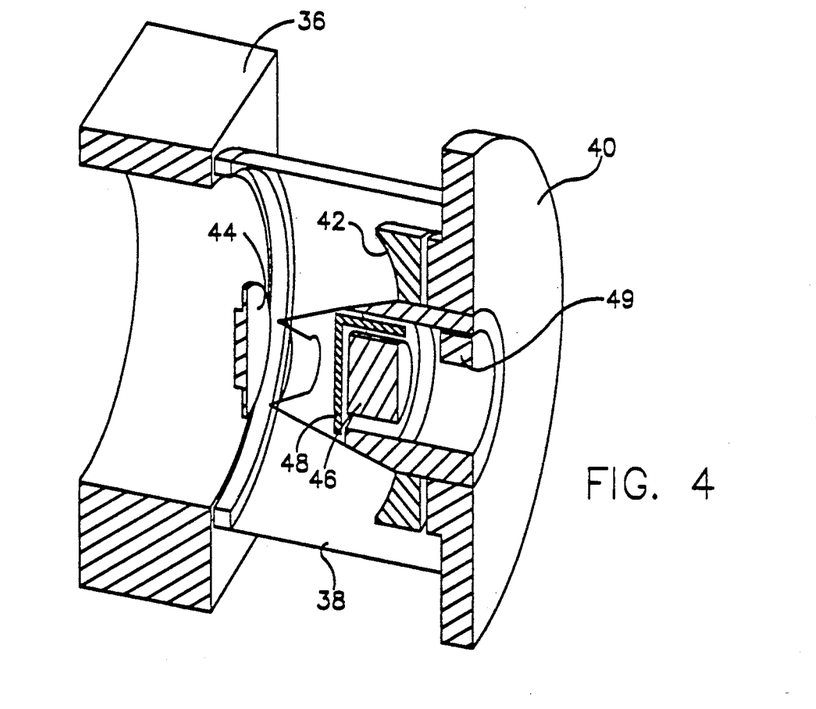
FIG. 4 is a cross-sectional view of the Cassegrain infrared telescope shown in FIG. 3.

Referring now to FIGS. 3 and 4, a commercially available embodiment of the Cassegrain infrared telescope 26 is shown. The exterior of the infrared telescope 26 comprises a front mount 36, an optical housing tube 38 connected at one end to the mount 36, and a back plate 40 connected to the other end of the tube 38.

The front mount 36 defines the front portion of the infrared telescope 26 and also provides the means of mounting the infrared telescope 26 onto the turntable 28. The exterior portion of the front mount 36 is essentially rectangular in shape and has mounting tabs 37 along the lower surface. The front mount 36 has a substantially circular opening 41, which extends from front to rear through the front mount 36, through which infrared radiation may enter the telescope assembly 26. A primary mirror 42 is mounted on the interior portion of the back plate 40 and reflects infrared radiation onto a secondary mirror 44, which is supported in position by a spider 45. The secondary mirror 44 then reflects the radiation and directs it onto an infrared detector 46, which is selectively covered by a shutter 48. The infrared detector 46 may comprise any of a plurality of infrared detectors. In the preferred embodiment, the detector 46 comprises a Model 2M Thermopile Detector commercially available from Dexter Research Center, Inc., 7300 Huron River Drive, Dexter Michigan 48130. This detector comprises an array of thermocouples, arranged in circular fashion, with one end of the thermocouple array covered with lampblack, an infrared absorbing material. The output of the thermocouples of the detector 46 is provided to the electronic assembly 34 for processing as will be later described. The detector 46 also includes a temperature sensor, (not shown) preferably thermistor, connected at the other end of the thermocouples to measure the reference temperature of the thermocouples. The temperature sensor provides a temperature reference signal to the electronic assembly 34.

In operation, infrared radiation enters the infrared telescope assembly 26 through the circular opening 41 and is transmitted through the optical housing tube 38 onto the primary mirror 42. The primary mirror 42 concentrates and reflects the radiation onto the secondary mirror 44 which in turn reflects the concentrated radiation onto the detector 46. The shutter 48 and a shutter motor 49, is provided whereby the shutter 48 may selectively cover the infrared detector 46 thereby preventing the measurement of incident infrared radiation. The shutter motor 49 is connected to the electronic assembly 34 for control purposes. During the period where the shutter 48 covers the detector 46, the internal temperature sensor provides a temperature signal from the detector 46 to the electronic assembly 34 thereby providing a means to calibrate the output of the infrared detector 46 to compensate for any electrical or temperature offset of the detector 46.

Figure 5:
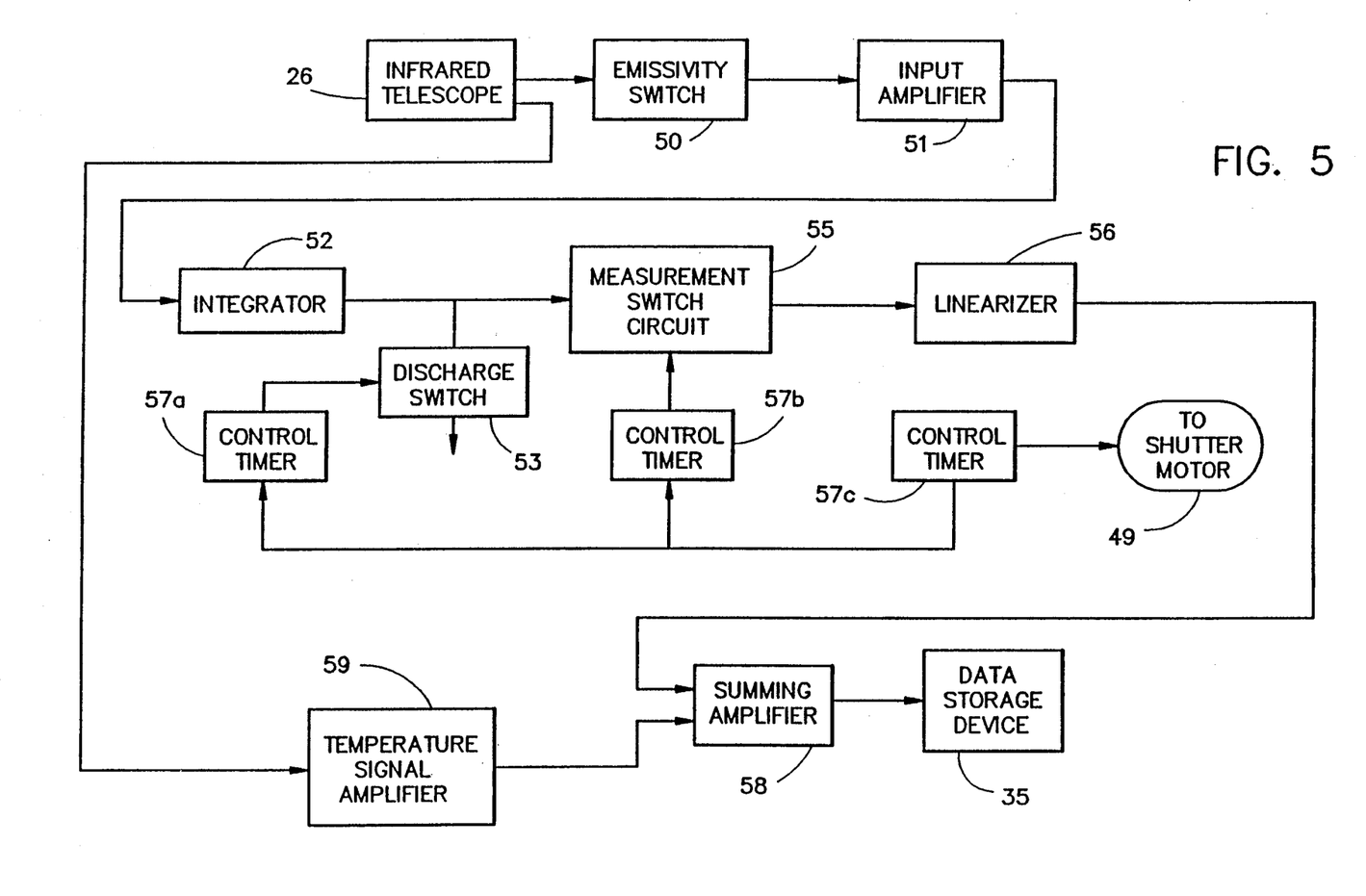
FIG. 5 is a block diagram of one embodiment of the electronic control circuit for use with a scanning infrared telescope.

Referring now to FIG. 5, a block diagram for the circuit of the electronic assembly 34 is shown in greater detail. The output from the infrared telescope; corresponding to the measured infrared radiation at the infrared detector 46, is provided to a preamplifier 50 and then to an emissivity circuit 51. The emissivity circuit 51 comprises an emissivity switch and an emissivity amplifier. The emissivity switch provides means to adjust the gain of the emissivity amplifier. In the preferred embodiment, the emissivity switch is a thumbwheel switch, adjustable by the user, having a 2-digit readout indicative of the selected gain of the emissivity amplifier. If a value of 0.99 is chosen, then the emissivity amplifier has a gain of one, but if a 0.1 is chosen the amplifier has a gain of 10. Thus, the emissivity switch selects the gain of the input amplifier 51 so that the output of the emissivity circuit 51 is adapted to match the emissivity of the crop whose temperature is to be measured. In operation, the user could either adjust the emissivity to a known value, or determine it experimentally. For example, he may select 0.96 as the known emissivity value for certain crops. Alternatively, the user could measure the temperature of the crop by any conventional means, and then adjust the emissivity switch until the system 15 outputs a temperature that is substantially equivalent to that measured conventionally.

The output of the emissivity amplifier is then provided to a filter 52, which in the preferred embodiment is a four pole active filter, which filters high frequency noise from the detector 46. In the preferred embodiment, the filter 52 has a cut-off frequency (3dB) of 10Hz. The output of the filter 52 is provided to an auto zero circuit 53. The purpose of the auto zero circuit 53 is to adjust for the "zero" value of the detector 46, that is, it provides an offset equal to the value of the detector when the shutter 48 is closed over the detector 4.

The auto zero circuit 53 also comprises a zeroing switch, connected to a first control timer 54. The zeroing switch, when closed, completes a circuit to ground so that a capacitor within the zeroing circuit has a voltage indicative of the voltage output from the filter 52. Typically, the zeroing switch is closed during the time that the shutter is closed, so that the voltage on the capacitor is indicative of the output of the infrared detector 46 when the shutter is closed, a value representative of the optical housing and shutter temperature, and electrical zero shifts. The capacitor is also connected to a high impedance buffer within the circuit 53. When the zeroing switch is open, the voltage on the capacitor reverses, causing an automatic bias of the input to the auto zero circuit 53. The zeroing switch is open when the shutter is open and receiving infrared radiation. Thus, the output of the infrared detector 46 is biased for any signal present due to the optical housing temperature and electrical zero shifts, so that the output of the high impedance buffer is indicative only of the infrared radiation incident upon the detector.

The circuit 53 also comprises a cutoff switch controlled by second control timer 55. One side of the cutoff switch is connected to the output of the high impedance buffer, and the other side of the switch is connected to a second high impedance buffer which provides the output of the auto zero circuit 53, and also to a capacitor which holds the voltage value at the output of the second buffer when the cutoff switch is open. When the cutoff switch is open, the output of the first buffer is isolated from the output of the second buffer zeroing switch is closed. The input of the second buffer is also connected to a capacitor which holds the voltage at the output of the auto zero circuit during the time that the cutoff switch is open. When the cutoff switch is closed, the output of the first buffer is connected to the input of the second buffer. As a result, when the zero switch is open, and the cutoff switch is closed, the voltage at the output of the auto zero circuit 53 is indicative of the infrared radiation incident upon the infrared detector 46.

Figure 5A:
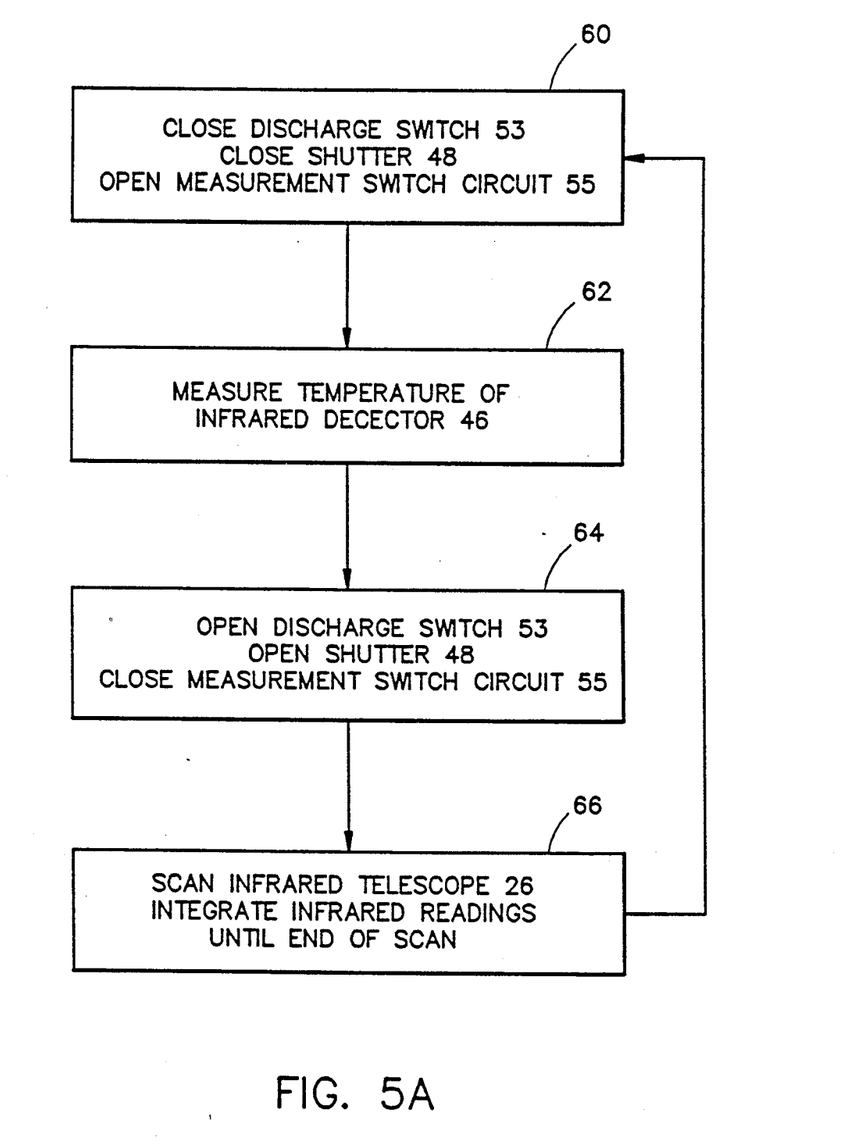
FIG. 5A is a flow chart depicting a sequence of operation of the scanning infrared telescope.

The sequence for one complete scan of the scanning system of the present invention is described more fully with respect to FIG. 5A. In general, switching of the zeroing switch and the cutoff switch is controlled by the first timer 54, and the second timer 55, respectively. The timers 54,55 are controlled by a third timer 56, which also controls the opening and closing of the shutter 48 by the shutter motor 49. Beginning at the start 62, it is assumed that the integration constant has been selected. The scanning motor 32 is actuated, and the turntable 28 rotates the telescope 26 back and forth so that it scans the field of view. In the block 64, the shutter is closed by the third control timer 56, which is a free-running multivibrator preferably having a eight second period and a 50% duty cycle. When the shutter is closed, the third timer 56 actuates the first timer 54 so that the zeroing switch is closed, and also actuates the second timer 55 so that the cutoff switch is open. Thus, a reference value is placed on the capacitor within the auto zero circuit. When the shutter is open, the third timer 56 actuates the first timer 54 so that the zeroing switch is open, and actuates the second timer 55 so that the cutoff switch is open, and thereby provides the output of the infrared detector 46 to the linearizer 57. Preferably, the first timer 54 comprises a four second one-shot that turns off the zeroing switch during the shot, and the second timer 55 also comprises a four second one-shot that turns off the cutoff switch during the shot. The sequence shown in FIG. 5A occurs substantially continuously while the telescope 26 scans the field. It is not necessary to stop the scanning to make measurements because the output of the system, as will be described, is available substantially continuously.

Referring to FIG. 5, the output of the auto zero circuit 53 is then directed to a linearizer 57. The linearizer 57 is provided because the output voltage of a typical detector 46 is non-linear over the temperature range. To compensate for the non-linearity, the linearizer 57 is an amplifier that has a gain that varies with voltage.

Thus, the linearizer 57 is an amplifier with a gain curve designed to produce a voltage at its output that is a linear function of temperature produced by infrared radiation incident upon the detector 46. The curve is determined from experimentally observed characteristics of the infrared detector 46, and the gain at each temperature is adjusted to provide a voltage output that is linear with temperature. Preferably, the linearizer 57 comprises a plurality of voltage comparators and resistors, implemented as a ladder network, to generate a substantially linear output over the temperature range. The linearizer 57 is easily constructed by one skilled in the art with a knowledge of the characteristics of the particular infrared sensor and a circuit diagram is therefore not provided.

The linear output from the linearizer 57 is provided as an input to a summing amplifier 58. A second input of the summing amplifier 58 is connected to the output of a temperature signal amplifier 59 which buffers and amplifies the output of the internal temperature sensor in the detector 46 of the infrared telescope 26. The summing amplifier 58 sums the output of the linearizer 57 with the output of the temperature signal amplifier 59 to adjust the reading of the detector 46 for thermal offset and thereby generate an output signal that is indicative of the temperature of the measured crop. The output of the summing amplifier 58 is directed to an integrator 60, which integrates the voltage of the output of the summing amplifier 58. The integrator 60 has a time constant which is determined by the integration time constant selector 39. The time constant selector 39 determines the rate of decay of the integrated voltage. For example, the selector 39 may be adjusted for a few seconds to integrate a single scan of the telescope 26. The selector 39 may also be adjusted for 100 seconds, which includes several scans of the telescope 26. With the long integration time that includes several scans, temperature variations within the scanning range are averaged out so that an accurate reading can be obtained. Furthermore, the temperature measurements may be obtained substantially continuously.

The output of the integrator 60 may be connected to a storage device which either continuously or at periodic intervals records the output. In addition, a conventional display, such as a digital display 61, may be connected to the output of the integrator 60, to provide a visual temperature reading.

DETAILED DESCRIPTION OF THE STATIONARY EMBODIMENT OF FIGS. 6 THROUGH 11

In another embodiment of the present invention, an infrared temperature sensing system 15 is provided for measuring the temperature of a crop growing in a field. This embodiment provides a wide field of view yet does not require the additional elements such as the turntable 28, the drive belt 30 and the scan motor 32 as shown in FIG. 2. In this embodiment, the infrared telescope 26 is replaced by a novel sensor head block 80 which advantageously provides a wide, rectangular field of view.

Figure 6:
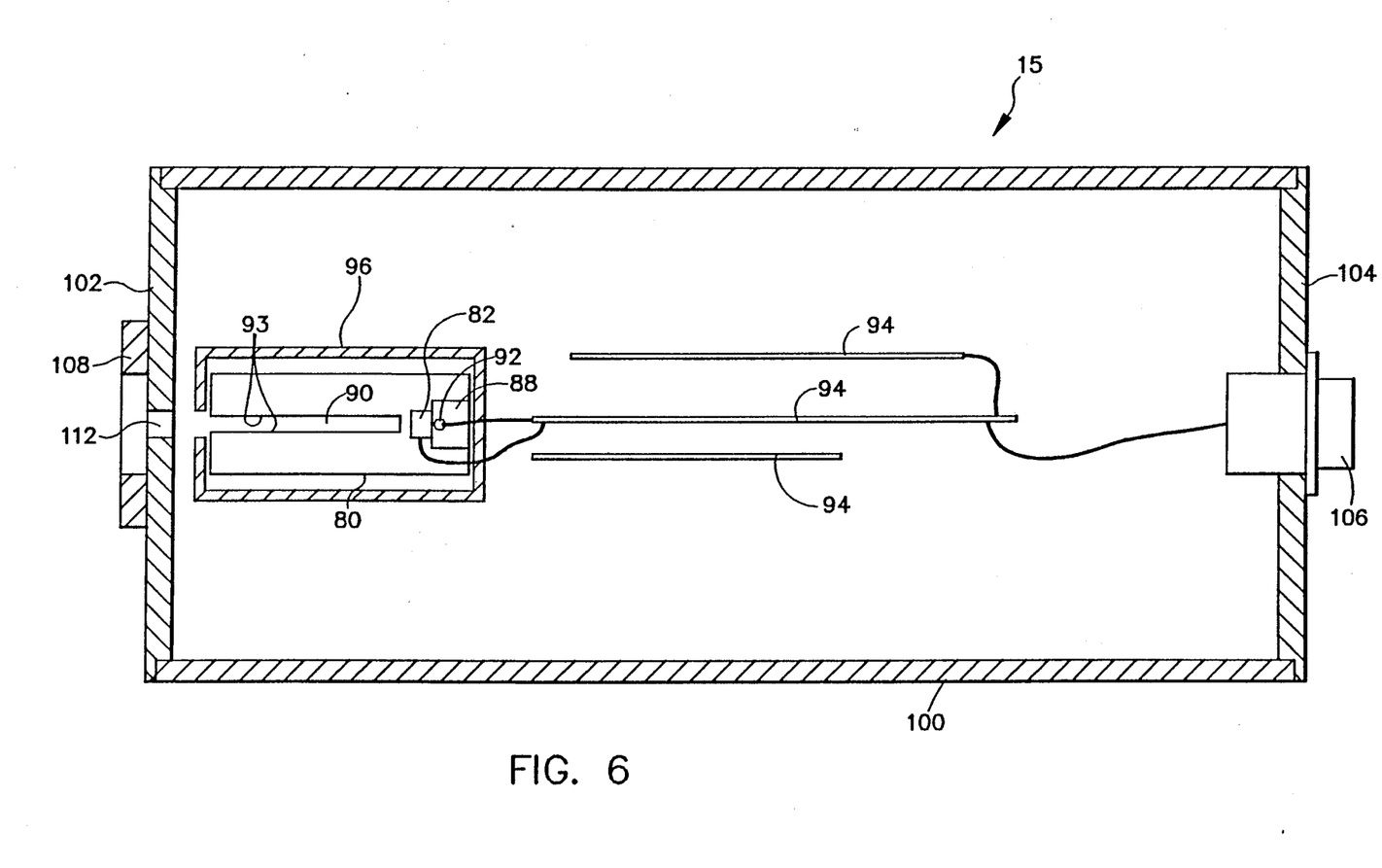
FIG. 6 is a sectional side view of the instrument housing structure of FIG. 1 showing a second embodiment of a foliage infrared thermometer comprising a stationary sensor head block having a wide field of view infrared thermometer in accordance with the invention.
Figure 7:
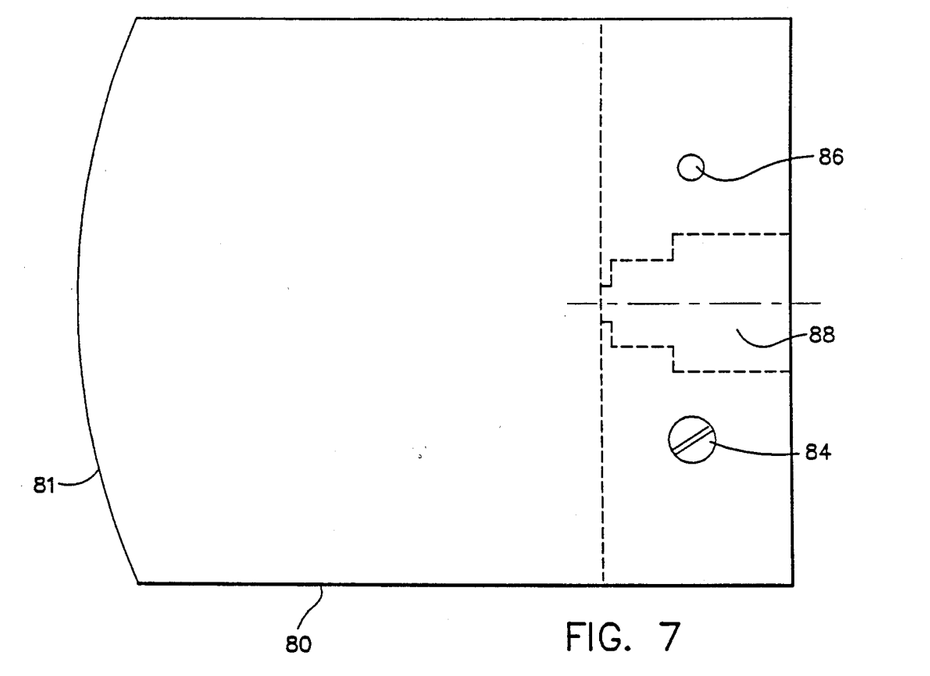
FIG. 7 is a top view of one embodiment of the stationary sensor head block of FIG. 6.
Figure 8:
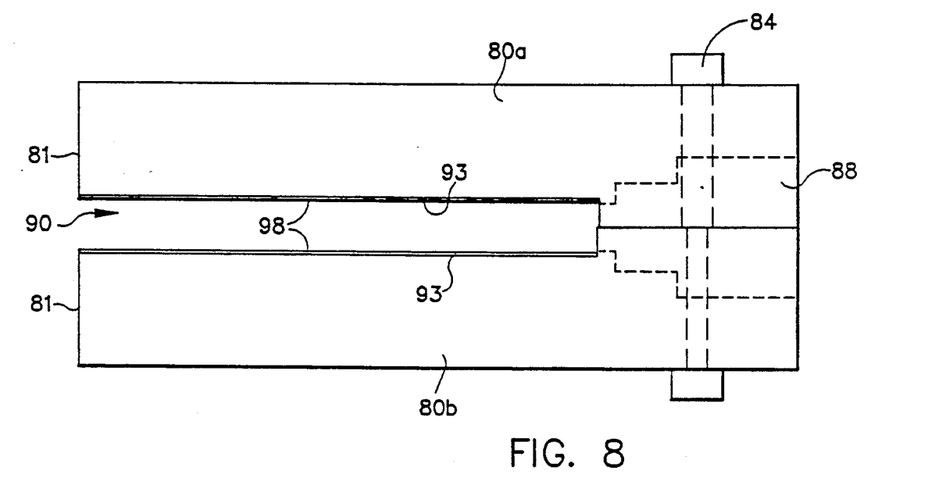
FIG. 8 is a side view of one embodiment of the stationary sensor head block of FIG. 6.

The sensor head block 80, shown in more detail in FIGS. 6, 7 and 8, preferably comprises a substantially rectangular block with the forward face 81 having a slight outward curvature. The sensor head block 80 is preferably comprised of a top block 80a and a lower block 80b. The top block 80a and lower block 80b are retained as a unit by a plurality of bolts such as 84 near the rear portion of the sensor head block 80. The bolts 84 pass through a plurality of bore holes such as a hole 86 provided in the sensor head block 80. A cavity 88 extends a short distance inward from the rear face of the sensor head block 80 toward the front face 81. An aperture 90 is formed between the top block 80a and the lower block 80b and extends from the front face 81 to the cavity 88. The aperture 90 defines the range from which infrared radiation is collected. Preferably, the aperture is rectangular, and has a width that is at least four times its height, and preferably, the aperture has a height of 4° to 6° and a width of 50°.

An infrared detector 82 is provided at the rear end of the aperture 90. The infrared detector 82 is positioned in the cavity 88 and aligned with the aperture 90 to sense infrared radiation from within the collection range of the aperture 90. The infrared detector 82 may comprise any of a plurality of infrared detectors. In the preferred embodiment, the detector 82 comprises a Model 2M Thermopile Detector commercially available from Dexter Research Center, Inc., 7300 Huron River Drive, Dexter Michigan 48130. This detector comprises an array of thermocouples, arranged in circular fashion, with one end of the thermocouple array coated with lampblack, an infrared absorbing material. The output of the thermocouples of the detector 82 is provided to a signal processing circuit 94 for processing as will be later described. The signal processing circuit 94 preferably comprises a plurality of electrically interconnected circuit boards as shown in FIG. 6.

A block temperature sensor 92, preferably a thermistor, is connected to the sensor head block 80 to sense the temperature of the head block 80, and the reference temperature of the thermocouples. Preferably, the block 80 comprises a thermally conductive material so that the temperature sensed by the sensor 92 is indicative of the temperature throughout the block 80. Futhermore, it is preferable that a lining 93 of the aperture 90 be comprised of a thermally conductive material having a low emissivity to ensure that the head block 80 temperature is uniform throughout the lining 93, and that infrared radiation incident upon the lining 93 is substantially reflected. The thermally conductive material on the lining 93 and the thermal conductivity of the block 80 prevents the generation of hot-spots on the aperture 90 which would emit infrared radiation and thereby distort the foliage temperature reading.

The output of the infrared detector 82 is provided to the signal processing circuit 94. The circuit is connected to the infrared detector 82 and also to the block temperature sensor 92, for providing an output responsive to the crop temperature. The signal processing circuit 94 is more fully discussed below.

To further prevent external variations in the temperature of the. environment from affecting the measurement, an external jacket 96 is provided that substantially surrounds the sensor head block 80. The jacket 96 provides an opening coincident with the aperture 90 on the front face of the sensor head block 80 so that infrared radiation may enter the aperture 90. Smaller openings in the jacket 96 permit the output of the infrared detector 82 and the temperature sensor 92 to be accessed. The jacket 96 comprises a low emissivity insulating material such as aluminum with the outside surface coated with gold. Because the sensor head block 80 is insulated from the outside environment, the temperature throughout the block 80 tends to remain substantially constant and uniform.

Figure 9:
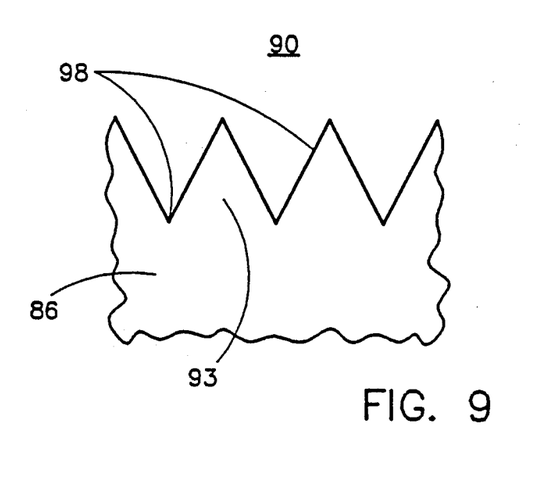
FIG. 9 is a expanded view of internal grooves of the sensor head block of FIG. 6 in accordance with the invention.

In the preferred embodiment, the lining 93 of the aperture 90 is further modified to reduce infrared radiation originating from outside the collection range of the aperture 90 from being reflected from the lining 93 to the infrared detector 82. The surface of the aperture 90, so modified, is illustrated in FIG. 9 where the modification preferably includes forming a plurality of grooves 98 in the surface of the aperture 90 so that the grooves 98 are substantially perpendicular to the direction of radiation from the crop to the infrared detector 82. The grooves 98 act as a infrared trap by baffling any incident radiation that is not substantially within the angle defined by the aperture 90 and the infrared detector 82.

Figure 10:
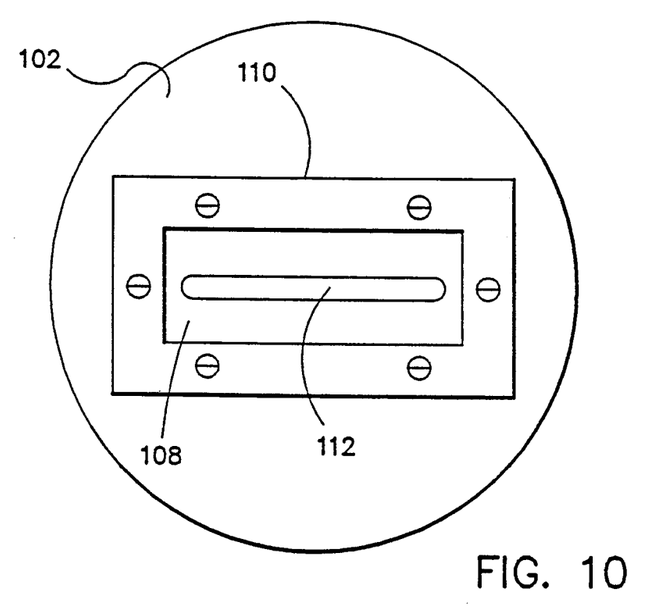
FIG. 10 is a front view of one embodiment of instrument housing structure of FIG. 6.

Referring to FIGS. 6 and 10, the stationary embodiment of the infrared temperature sensing system 15 is preferably housed in a cylindrical housing 100, which shields the sensor head block 80, the temperature sensor 92 and the signal processing circuit 94 from outdoor elements. The housing 100 has a front face plate 102 and a rear face plate 104. The rear face plate 104 is provided with a port 106 so that the output of the signal processing circuit 94 may be remotely accessed. As shown in FIG. 10, the front face plate 102 is provided with a rectangular window 108 attached to the front face plate 102 by a frame 110. The window 108 is advantageously constructed from polypropylene film and positioned over a radiation entrance 112. The radiation entrance 112 is provided in the face plate 102 behind the protective window 108. The radiation entrance 112 is preferably configured as substantially rectangular in accordance with the shape of the aperture 90 in order to restrict the amount of infrared radiation incident upon the block 80.

When the infrared temperature sensing system 15 is in operation, infrared radiation from the sensed crop within the sensed angle passes through the window 108, through the radiation entrance 112 and then through the opening in the jacket 96. Thus, radiation within the sensed angle that is substantially parallel with the horizontal axis of the housing 100 will be substantially transmitted to the infrared detector 82. Radiation that is non-parallel with the horizontal axis of the housing 100 will be either blocked by the radiation entrance 112 or substantially trapped and dissipated by the grooves 98 located in the aperture 90.

The infrared temperature sensing system 15 may be permanently mounted in a field to monitor foliage temperature because the housing 100 protects the instrument from the elements. The housing 100 may be provided with mounting brackets (not shown) or other means for mounting the housing 100 in the field such as shown in FIG. 1.

Figure 11:
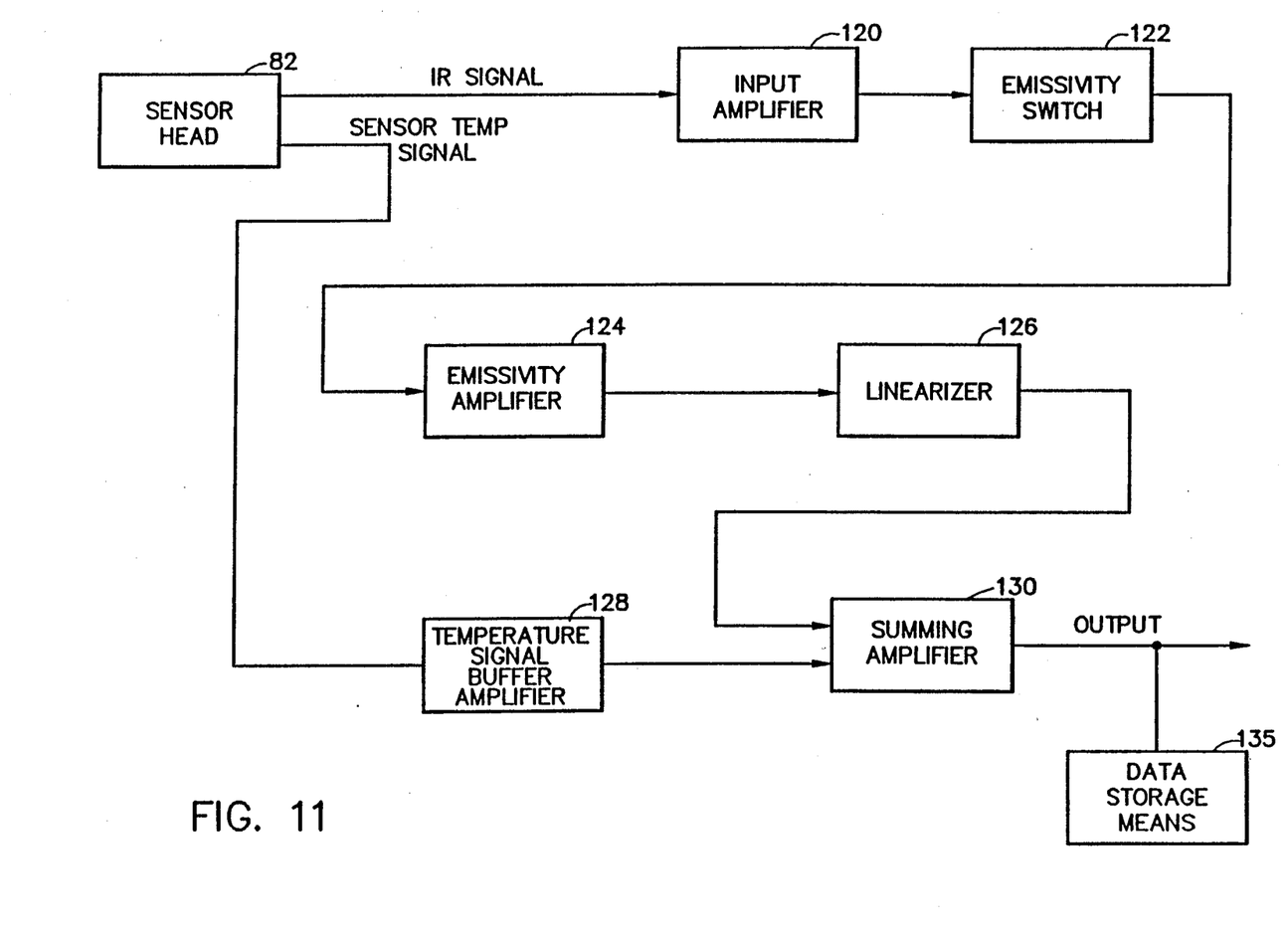
FIG. 11 is a block diagram of electronic circuitry for use with the embodiment of the invention shown in FIG. 6.

Referring now to FIG. 11, the output of the infrared detector 82 and block temperature sensor 92 are provided from the sensor head 80 to a signal processing circuit 94. The infrared detector 82 provides a proportional electrical output that combines the temperature of the crop and the sensor head block 80, while the temperature sensor 92 provides an output proportional to the temperature of the sensor head block 80. The output of the infrared detector 82 is adjusted to reflect the temperature of the sensor head block 80 by the signal processing circuit 94 and an output is provided that is responsive to the crop's foliage temperature.

The signal processing circuit 94, shown in FIG. 11, comprises an input amplifier 120, an emissivity switch 122, which controls the gain of an emissivity amplifier 124, to adjust for variations in the emissivity of the measured object, identical with the emissivity circuit 51 as described previously with respect to FIG. 5. The circuit 94 further comprises a linearizer circuit 126, a summing amplifier 130, a temperature signal amplifier 128 and a data storage device 135. The circuit 94 in the preferred embodiment is substantially similar to a circuit provided in the Infrared Temperature Control System, Model 2100, commercially available from Telatemp Corporation, P.0. Box 5160, Fullerton, CA 92635-0160.

In operation, the infrared detector 82 generates a signal that is provided to the input amplifier 120 which amplifies the small signal output of the infrared detector 82. The amplified signal is provided to an emissivity switch 122 and emissivity amplifier 124 whereby the amplification of the signal may be controlled to adjust for various environmental parameters, such as the emissivity of the crop. The output of the emissivity amplifier 124 is provided to a linearizer 126. As stated above with reference to FIG. 5, the linearizer 126 is required because the output voltage of the typical detector 82, is typically non-linear over the temperature range, and such a linearizer can be easily constructed by one skilled in the art.

The output of the linearizer 126 is added to the output of the temperature signal amplifier 128 at a summing amplifier 130. The input to the temperature signal amplifier 128 is derived from the temperature sensor 92 and represents the temperature of the sensor head block 80. The effect of adding the output of the temperature sensor amplifier 128 with the output of the linearizer 126 is to generate a signal that represents the temperature of the foliage temperature of the crop. This temperature signal may be captured and stored on a data storage device 135. The data capture may be continuous or at periodic time intervals.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. An agriculture thermometer for measuring the temperature of a crop growing in a field, the crop emitting infrared radiation in an amount dependent upon the temperature of the crop, said thermometer comprising:
    an infrared detector for sensing the amount of infrared radiation emitted from the crop;
    means for defining a substantially elongated oval field of view for radiation incident upon the infrared detector, said elongated oval field of view having a width at least four times its height; and an aperture having a size and shape to substantially exclude infrared radiation not within said field of view, said aperture having a stationary position with respect to the crop.

2. The agriculture thermometer as claimed in claim 1, wherein said thermometer includes a circuit providing an output responsive to the temperature of the crop, and further wherein said circuit comprises a means for storing the value of said output at periodic time intervals.

3. The agriculture thermometer as claimed in claim 1, wherein said thermometer includes a turntable rotatable through a selected angular rotation, said infrared detector being mounted on said turntable so that said detector scans said substantially rectangular area in one sweep through said selected angular rotation.

4. The agricultural thermometer as claimed in claim 3, wherein said thermometer includes a integrating circuit for summing the output of the infrared detector during one sweep of said angular rotation.

5. The agricultural thermometer as claimed in claim 1, wherein said elongated oval field of view has a width that is at least ten times its height.

6. The agricultural thermometer as claimed in claim 5, wherein the elongated oval field of view is approximately 4° in height and approximately 50° in width.

7. An agricultural thermometer for measuring the temperature of a crop growing in a field, said thermometer comprising:
    an infrared telescope assembly including:
        an infrared detector, and
        an optical assembly for directing radiation from selected angles to said infrared detector;
    a turntable, said infrared telescope assembly being mounted on said turntable;
    means for rotating said turntable through a selected angular rotation;
    a structure housing said infrared telescope assembly and said turntable, said structure remaining relatively stationary when said infrared telescope assembly is rotated; and
    a circuit, including means for integrating the output of the infrared detector during at least one sweep of said angular rotation, said circuit providing an output responsive to the temperature of the crop scanned by said telescope assembly.

8. The crop agricultural thermometer as claimed in claim 7, wherein said circuit comprises a means for storing, at periodic time intervals, the output responsive to the crop temperature measurements.

9. The agriculture thermometer as claimed in claim 7, wherein the infrared telescope detects infrared radiation within a conical field of view having a total angle of view that is substantially less than the selected angle of rotation of the turntable.

10. The agricultural thermometer as claimed in claim 7, further comprising a means for mounting the thermometer in a field.

11. A method of measuring crop temperature, comprising the steps of:
    first providing an infrared detector mounted on a rotating turntable;
    said infrared detector and said rotating turntable being located within a stationary housing;
    second, sweeping the turntable through a selected angle of rotation;
    third, integrating the output of the infrared detector substantially simultaneously with the sweep of the second step; and
    fourth, providing an output responsive to the crop temperature.

12. The method of measuring temperature of claim 11, further comprising an additional step following the fourth step:
    fifth, calibrating the infrared detector to compensate for the temperature of the detector itself.

* * * * *